United States Patent [19]

Roberts

[11] Patent Number: 5,741,502
[45] Date of Patent: *Apr. 21, 1998

[54] HOMOGENEOUS, ESSENTIALLY NONAQUEOUS ADJUVANT COMPOSITIONS WITH BUFFERING CAPABILITY

[75] Inventor: Johnnie R. Roberts, Memphis, Tenn.

[73] Assignee: Helena Chemical Co.

[*] Notice: The term of this patent shall not extend beyond the expiration date of Pat. Nos. 5,178,795, 5,392,791 and 5,580,567.

[21] Appl. No.: 731,415

[22] Filed: Oct. 15, 1996

Related U.S. Application Data

[63] Continuation-in-part of Ser. No. 394,839, Feb. 27, 1995, Pat. No. 5,580,567, and a continuation-in-part of Ser. No. 960,894, Oct. 14, 1992, Pat. No. 5,393,791, and a continuation-in-part of Ser. No. 554,359, Jul. 19, 1990, Pat. No. 5,178,795.

[51] Int. Cl.$^6$ .......................... A01N 25/02; A01N 27/00; B01J 13/00
[52] U.S. Cl. .................. 424/405; 71/DIG. 1; 252/312; 252/356; 504/334; 514/762; 514/941
[58] Field of Search ..................... 252/312, 356; 71/DIG. 1; 514/762, 941; 424/405; 510/437; 504/334

[56] References Cited

U.S. PATENT DOCUMENTS

| | | | |
|---|---|---|---|
| 2,380,166 | 7/1945 | Griffin | 252/312 X |
| 2,528,136 | 10/1950 | Goldstein et al. | 252/356 |
| 3,071,550 | 1/1963 | Altscher et al. | 252/354 |
| 3,894,149 | 7/1975 | Mast | 71/DIG. 1 |
| 3,898,075 | 8/1975 | Freund et al. | 71/111 |
| 3,997,322 | 12/1976 | Ratledge | 71/93 |
| 4,097,403 | 6/1978 | Tsutsumi et al. | 252/DIG. 1 |
| 4,224,049 | 9/1980 | Devisetty et al. | 71/DIG. 1 |
| 4,313,847 | 2/1982 | Chasin et al. | 252/356 |
| 4,637,830 | 1/1987 | Dyer et al. | 71/105 |
| 4,755,207 | 7/1988 | Bannon | 71/DIG. 1 |
| 4,834,908 | 5/1989 | Hazen et al. | 252/356 |
| 4,851,421 | 7/1989 | Iwasaki et al. | 514/941 X |
| 4,944,949 | 7/1990 | Story et al. | 514/914 X |
| 4,966,728 | 10/1990 | Hazen | 252/356 X |
| 5,169,968 | 12/1992 | Rice | 554/193 |
| 5,178,795 | 1/1993 | Roberts | 252/356 |
| 5,206,021 | 4/1993 | Dookhith et al. | 424/405 |
| 5,393,791 | 2/1995 | Roberts | 514/762 |
| 5,580,567 | 12/1996 | Roberts | 424/405 |

FOREIGN PATENT DOCUMENTS

| | | | |
|---|---|---|---|
| 703607 | 2/1965 | Canada | 71/DIG. 1 |

OTHER PUBLICATIONS

Rose et al.: *The Condensed Chemical Dictionary*, Sixth Edition, Reinhold Publishing Corp., New York (1961), p. 858.

Simanton et al.: "Recommended Specifications for Citrus Spray Oils in Florida", Reprint from vol. 79 of Proceedings of the Florida State Horticultural Society, Miami, Oct. 24–27, 1966, pp. 26–30.

Paraspread Plus Manufactured by Custom Chemicides (1993).

Armul 1372 Manufactured by Witco Corporation (Jan. 1989).

*Primary Examiner*—Richard D. Lovering
*Attorney, Agent, or Firm*—Connolly & Hutz

[57] ABSTRACT

A homogeneous, essentially nonaqueous adjuvant composition containing at least one spray oil selected from the group consisting of:

(a) vegetable oils;
(b) fatty acids and blends thereof;
(c) esterified fatty acids or blends thereof;
(d) saponified fatty acids or blends thereof;
(e) N,N-dimethylamide of the formula $RCON(CH_3)_2$
wherein R is an alkyl chain derived from fatty acids having about 6 to about 18 carbon atoms;
(f) polybutenes
(g) alpha or beta pinene,
(h) thymol,
(i) d-limonene and
(j) jojoba bean oil, (2) a surfactant in an effective amount to provide emulsification of said composition and (3) a buffering agent wherein said buffering agent can also be the same ingredient as said oil or said surfactant and said buffering agent reduces the pH of said composition to about 7 or below.

22 Claims, No Drawings

HOMOGENEOUS, ESSENTIALLY NONAQUEOUS ADJUVANT COMPOSITIONS WITH BUFFERING CAPABILITY

CROSS REFERENCE TO RELATED APPLICATION

This application is a continuation-in-part of Ser. No. 08/394,839, which was filed Feb. 27, 1995, and is now issued as U.S. Pat. No. 5,580,567 and is a continuation-in-part of Ser. No. 07/960,894, which was filed Oct. 14, 1992 and is now issued as U.S. Pat. No. 5,393,791 and a continuation-in-part of Ser. No. 07/554,359, which was filed Jul. 19, 1990 and is now issued as U.S. Pat. No. 5,178,795.

The present invention relates to the field of agricultural, forestry, turf, ornamental, industrial, aquatic, rights-of-ways and other applications where pesticides are used and, more specifically, to adjuvant compositions which improve the chemical and physical properties of a pesticide such as an herbicide, insecticide or fungicide.

BACKGROUND OF THE INVENTION

In order to enhance or modify the chemical and/or physical characteristics of certain pesticides, certain materials are added to form a mixture for spraying. Generally referred to as adjuvants, these materials have no pesticidal activity of their own. Since spray application can be critical to the performance of the agricultural chemical, adjuvants are added to reduce application problems such as chemical stability, incompatibility, solubility, suspension, foaming, drift, evaporation, volatilization, phytotoxicity, surface tension, droplet size and coverage. They can, depending on their type, enhance wetting, spreading, sticking, emulsifying, dispersing and biological activity. Adjuvants include wetting agents, crop oil concentrates, spreaders, stickers, buffering agents, foaming and anti-foaming agents, dispersing agents and drift control agents. Over 200 EPA-registered pesticides have specific recommendations on their labels for adjuvant use. These are recommended for one of two reasons—or both. First, to enhance biological activity of the pesticide and second, to reduce, minimize or eliminate spray application problems as noted previously. There are several different types of adjuvants recommended. To achieve consistent, effective results from them, the user must first select the desired type of adjuvant and then the appropriate product within that specific type for use with a particular pesticide and then use that product at recommended rates.

It is known that petroleum hydrocarbon spray oils increase the efficacy of herbicides, fungicides and other pesticides by enhancing the deposition characteristics and wetting and spreading of the spray solution resulting in a more even and uniform spray deposit or by increasing the biological effect of certain pesticides. Other oils such as esterified vegetable oils and once-refined vegetable oils are known to exhibit similar properties. Such spray oils can increase penetration and slow evaporation. Paraffin based spray oil is a petroleum oil used as dormant spray, summer oil, carrier for pesticides or an adjuvant to increase the efficacy of agricultural chemicals.

In U.S. Pat. No. 3,977,322, an agricultural spray oil composition comprising a major amount of a petroleum oil and a minor amount of a vegetable oil is disclosed as providing a particularly improved carrier which enhances the effectiveness of selective herbicides.

A synergistic herbicidal composition is disclosed in U.S. Pat. No. 4,755,207 and comprises a non-phytotoxic crop oil, a surfactant, and hydrophobic mycoherbicide spore. The oils are once refined vegetable oils or highly refined paraffinic material. The surfactant can be anionic, cationic or nonionic.

A surfactant composition is disclosed in U.S. Pat. No. 4,317,847 issued to Chasin. Chasin discloses a solvent having a high aromatic content above 95% which corresponds to a very low UR value.

Some applications require the separate addition of buffering agents to adjust the pH of alkaline waters used to make up the spray solutions. The buffering agents regulate solution pH to avoid hydrolysis of pesticides that tend to decompose in alkaline spray solutions. Generally, the spray's pH should be adjusted to a range of 4 to 6 or slightly acidic. Known buffering agents include alkyl aryl polyethoxy ethanol phosphates and organic phosphatic acids as the principal functioning agents. Typically, such a buffering agent is added to the water which is then combined with the pesticide and any other adjuvants required.

U.S. Pat. No. 4,244,049 relates to aqueous-lower alkanol solutions containing alkylaryl polyoxethylene glycol phosphate esters which act as compatibility agents for mixtures of liquid fertilizer and pesticides. The solution contains about 20% methanol, about 16% water and about 64% of the phosphate ester.

A biocidal fine powder and an agricultural suspension containing the fine powder and an adjuvant are disclosed in U.S. Pat. No. 4,851,421. The adjuvant can be a polyoxyalkylene-type nonionic surface active agent or polyoxyalkylene alkyl or alkylaryl ether phosphates or their salts. The composition does not include any oil components.

It is advantageous to reduce the separate addition of each of the adjuvants to the herbicide or pesticide to save time and to reduce possibility of error in the amounts added since mixing is typically done in the field by unskilled workers. However, the components of an adjuvant composition must form a homogeneous liquid mixture, not a slurry or suspension. Otherwise, the amount of oil and surfactant in the spray will vary form use to use and these variations would adversely affect the physical properties of the spray. In the prior compositions, adjuvants such as buffering agents have been added to the water, then combined with the other adjuvants and the active ingredient because the phosphate compounds used as buffering agents are hydrophilic polar compounds. It is difficult to combine such compounds with oil and obtain a homogeneous composition having the desired spray uniformity and coverage.

It is the object of this invention to provide an essentially non-aqueous, single-phase adjuvant composition containing oil plus surfactant blend and which provides buffering capability. Even after the addition of alkaline water and pesticides, use of this composition reduces and/or maintains the pH of the spray mixture within a desired range to prevent hydrolysis of the pesticide.

SUMMARY OF THE INVENTION

The present invention is a homogeneous, essentially non-aqueous adjuvant composition comprising a spray oil, a surfactant and optionally a buffering agent in an amount to reduce the pH to below about 7. It is possible that the oil and/or surfactant component could be used in lieu of the buffering agent if the oil and/or surfactant can reduce the pH of the composition to below about 7. It is also possible that some oils, when coupled into water, could provide buffering on their own. When mixed with a pesticide, the composition provides one-step addition of the adjuvants to obtain a more uniform spread of the spray solution of the herbicide or pesticide, improved penetration and slower evaporation. The adjuvant can also be used as a pesticide or herbicide without the addition of any additional pesticide to the adjuvant. The presence of the buffering agent maintains the pH of the mixture within a desired range pH below about 7 in the presence of alkaline waters typically used in spray solutions.

DETAILED DESCRIPTION OF THE INVENTION

This invention is a homogeneous, essentially nonaqueous adjuvant composition having buffering capability. According to the process of this invention, the adjuvant composition comprises a spray oil and a blend of surfactants and optionally a buffering agent so that the pH of the composition to below about 7. The buffering agent is not necessary if the oil and/or surfactant can reduce the pH of the composition to below about 7.

The spray oils utilized in this composition should range from 85% UR to 100. Preferably, the oil in combination with one or more of the buffering agents below should be mixed with one or more of the surfactants below: in the range of about 5.0 to about 19.5% by weight.

One of the preferred homogeneous, essentially nonaqueous adjuvant composition comprises:

(1) at least one spray oil selected from the group consisting of:

(a) vegetable oils;
(b) fatty acids and blends thereof;
(c) esterified fatty acids or blends thereof;
(d) saponified fatty acids or blends thereof;
(e) N,N-dimethylamide of the formula
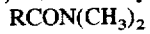
wherein R is an alkyl chain derived from fatty acids having about 6 to about 18 carbon atoms;
(f) polybutenes of the following formula

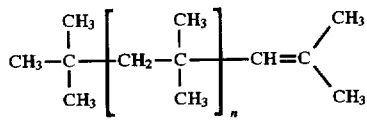

where n is a number from about 1 to about 50; and
(g) spray oils having a UR value from about 85% to 100, and (2) a surfactant in an effective amount to provide emulsification of said composition and optionally (3) a buffering agent in an amount sufficient to reduce the pH to below about 7. The buffering function could be performed by some of the oil or surfactant components.

The spray oils utilized in this composition do not need to have an unsulfonated residence (UR) value and include at least one of the following:

1. Vegetable oils:
the vegetable oils can be, but are not limited to vegetable seed oil or a mixture of vegetable seed oils, as they are known in the agricultural industry, crop seed oils which are produced from the particular crop from which their name is derived. Included in the vegetable oils suitable for the compositions of the present invention are cotton seed oil, canola, rapeseed, peanut oil, sunflower oil, linseed oil, safflower oil, soybean oil, corn oil, olive oil, coconut oil, tall oil or other seed oils and blends of the above oils such as cotton seed oil plus soybean oil; cotton seed oil plus peanut oil; cotton seed oil plus olive oil; corn oil plus linseed oil; corn oil plus soybean oil; as well as blends of any two or more of the above disclosed vegetable oils. The vegetable oils can be present in an amount from about 1 to about 99%, preferably from about 50 to about 99% and most preferably from about 80 to about 99%.

2. Fatty acids and blends thereof:
Such as, but not limited to saturated and unsaturated fatty acids of about 6 to about 18 carbon atoms. The fatty acids and blends can be present in an amount from about 1 to about 99%, preferably from about 50 to about 99% and most preferably from about 80 to about 99%. The fatty acids can be used without a buffering agent when they reduce the pH of the solution to about 7 or below. The fatty acids can be used without a buffering agent when they reduce the pH to below about 7.

3. Esterified fatty acids or blends thereof:
Such as, but not limited to saturated and unsaturated esters of about 6 to about 18 carbon atoms. The esterified fatty acids can be present in an amount from about 1 to about 99%, preferably from about 50 to about 99% and most preferably from about 50 to about 80%. The esterified fatty acids may also be derived from any of the vegetable oils previously mentioned.

The esterified fatty acids can be used without a buffering agent when they reduce the pH of the solution to about 7 or below. The esterified fatty acids can be used without a buffering agent when they reduce the pH to below about 7.

4. Saponified fatty acids or blends thereof:
Such as, but not limited to saturated and unsaturated soaps of about 6 to about 18 carbon atoms. The saponified fatty acids can be present in an amount from about 1 to about 99%, preferably from about 50 to about 99% and most preferably from about 50 to about 80%. The saponified fatty acids may also be derived from any of the vegetable oils previously mentioned. The saponified fatty acids can be used without a buffering agent when they reduce the pH of the solution to about 7 or below. The saponified fatty acids can be used without a buffering agent when they reduce the pH to below about 7.

5. N,N dimethylamides of the following formula:
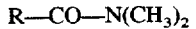
wherein R is an alkyl chain derived from fatty acids having about 6 to about 18 carbon atoms. The N,N dimethylamides can be present in an amount from about 1 to about 99%, preferably from about 50 to about 99% and most preferably from about 80 to about 99%.

6. Polybutenes:
The polybutenes that can be used are of the following formula:

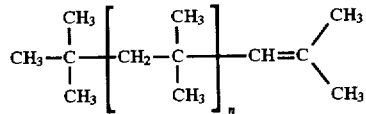

where n is a number from about 1 to about 50. The polybutenes can be present in an amount from about 1 to about 99%, preferably from about 50 to about 99% and most preferably from about 80 to about 99%.

7. Alpha or beta pinene.
8. Thymol.
9. d-limonene.
10. Jojoba bean oil.
11. Mixture of at least one of 1–10 above.

These 10 groups of oils can be a portion of the spray oil or the entire spray oil.

The spray oil is used in combination with one or more of the buffering agents and should be mixed with one or more of the surfactants below. However, a buffering agent is not required if the surfactant or oil can provide the properties to reduce the pH to below about 7. The surfactant is present in an effective amount to provide emulsification of the composition. The amount of the surfactant is usually in the range of about 5.0 to about 19.5% by weight. The preferred blend of surfactants include but are not limited to:

a) sorbitan fatty acid ester,
b) polyethoxylated derivative of a sorbitan fatty acid ester,
c) fatty alkanolamides of the formula

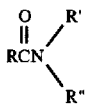

wherein R is an alkyl group having about 6 to about 25 carbon atoms; R and R" independently of one another are selected from the group consisting of hydrogen, —$CH_2CH_2OH$ or $$CH_2-CH-OH, \atop \phantom{CH_2-}CH_3$$

d) peg esters of the formula

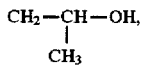

wherein R is a fatty alkyl having from about 2 to about 25 carbon atoms, R' is a fatty alkyl having from about 2 to about 25 carbon atoms or H and m is a number from 1 to about 100, e) silicone surfactants of the formula

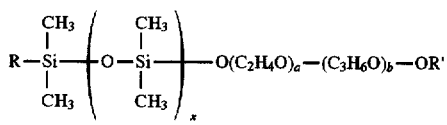

OR

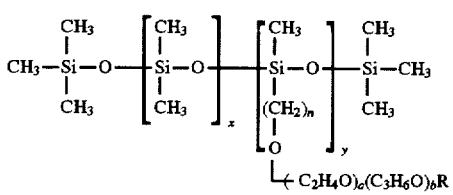

wherein R and R' independently from one another are hydrogen, alkyl having from 1 to about 20 carbon atoms, preferably 1 to 4 carbon atoms or an alkyl ester group having 1 to 20 carbon atoms, preferably 1 to 4 carbon atoms, x is a number from about 1 to about 100, preferably from about 1 to about 5, y is a number from about 1 to about 5, a is a number from about 3 to about 25, b is a number from about 0 to about 25, n is a number from about 2 to about 4 and f) ethoxylated fatty acids

wherein R is an alkyl group having from about 6 to about 25 carbon atoms, n is a number from 1 to about 100, g) alkyl ethoxylates
$RO(CH_2CH_2O)_xH$
wherein R is an alkyl group having from about 1 to about 50 carbon atoms and x is a number from 1 to about 100, h) alkylphenol ethoxylates

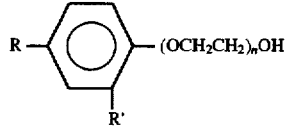

wherein R is H or an alkyl having from about 1 to about 20 carbons, R' is H or an alkyl having from about 1 to about 20 carbons and n is a number from 1 to about 100, i) polypropylene glycols

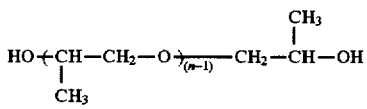

wherein n is a number from 1 to about 100, j) tristyrylphenol alkoxylates, k) amine ethoxylates

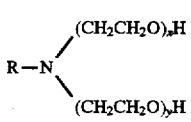

wherein x and y independently of one another are a number from about 1 to about 100 and R is an alkyl having from 1 to about 25 carbon atoms, l) N-Acyl Sarcosines and Sodium N-Acyl Sarcosinates,
m) alkylaryl polyethoxy phosphate ester,
n) alkylaryl polyethoxy carboxylate ester,
o) tristyrylphenol alkoxylate phosphate esters,
p) tristyrylphenol alkoxylate carboxylate esters,
q) Phosphate esters of block copolymers of ethylene and propylene oxide or
r) alkylpolyglucosides.

The preferred buffering agent are used in an amount up to about 10% by weight, preferably at about 0.5 to about 10% by weight in the formulation. The amount will be determined by the ability of the composition to reduce pH values of the pesticide spray mix to about 7 or less. The most preferred would be one in which the pH reduction could be accomplished by using no more than 0.5% by volume of the final composition.

The preferred buffering agents include, but are not limited to, a) alkylaryl polyethoxy phosphate ester, b) $C_1$–$C_6$ carboxylic acids, c) $C_1$–$C_6$ dicarboxylic acids, d) phosphoric acid, e) citric acid, f) glutaric acid, g) gluconic acid, h) lactic acid,
i) glycolic acid,
j) acrylic acid,
k) carboxylated alcohol ethoxylate, preferably of the formula R—O(CH$_2$CH$_2$O)$_x$H R is a carboxylic acid having from 1 to about 25 carbon atoms and x is from 1 to about 20 moles ethylene oxide,
l) ethoxylated alkylaryl phosphate esters;
m) ethoxylated alkylphenol carboxylate esters;
n) tristyrylphenol alkoxylate phosphate esters;
o) tristyrylphenol alkoxylate carboxylate esters;
p) fatty acids and blends thereof and
q) phosphate esters of block copolymers of ethylene and propylene oxide.

Additionally the spray oil used in the compositions of this invention can also contain agricultural spray oils which are petroleum hydrocarbon oil. The hydrocarbon oil is not required to be used in this invention. These spray oils are the refined fraction of petroleum oil and the preferred petroleum oil is a paraffin oil which is a blend of $C_{10}$–$C_{18}$ saturated aliphatic hydrocarbons. Spray oils can be characterized by specifications such as unsulfonated residue, API-gravity, distillation range and pour point. A high unsulfonated residue (UR) indicates a minimum of reactive material in the spray oil and the oil's degree of refinement. This UR value corresponds to about 100% minus the aromatic content. Kerosine, coal oil, naphtha and diesel fuel are all phytotoxic and exhibit low UR values due to their reactivity and therefore, they all have a high aromatic content. Paraffinic oils that have high UR values exhibit little or no phytotoxicity. A minimum of 92% UR is typically required for agricultural spray oils. A spray oil with a 31–34 API gravity indicates a high degree of paraffinic oil content. An API gravity value of 23 or less indicates an oil with aromatic and naphthenic constituents. As a result, such oils are more reactive and phytotoxic. The distillation range determines physical properties of spray oils. Also, a high boiling range is an indication of an oil's phytotoxicity. Lower boiling ranges indicate that the oil has an increased evaporation rate and lower tenacity.

Agricultural spray oils useful in the compositions of this invention have distillation ranges between about 400° to about 500° F. Pour point values reflect the wax content of spray oils. A high value indicates a large amount of wax in the oil. Waxes reduce the spreading and penetration properties of the spray oil. The spray oils used in the present invention have pour points no greater than about 20° F. Generally, oils having a distillation range of 400°–435° F. are used in adjuvants for fungicide and pesticide applications. Oils having a distillation range of about 445° to about 500° F. are employed in adjuvants applications directed at herbicides. As noted previously, the higher boiling oils have increased phytotoxicity which is useful when the objective is to enhance the effectiveness of some contact-type herbicides.

The following table illustrates typical specifications of spray oils useful in the compositions of this invention.

| Gravity API | 32.8 | 34.3 | 34.6 | 33.0 |
|---|---|---|---|---|
| (Density | 0.8608 | 0.8530 | 0.8515 | 0.8597 |
| Unsulfonated Residue % | 99.0 | 99.0 | 99.0 | 93–97 |
| Pour Point °F. Max | −5 | −5 | −5 | −5 |
| Distillation D1160 | | | | |

-continued

| °F. at 10 MM HG | | | | |
|---|---|---|---|---|
| 50% Recovered | 404 | 435 | 454 | 465–471 |
| Range 10–90% | 55 | 72 | 80 | |
| Viscosity CST C40° C. | 10.7 | 13.59 | 14.8 | 21.4 |
| SUS 100° F. | 60 | 70 | 82 | 112 |
| Flash °F. | 335 | 345 | 376 | 385 |
| Color | L0.5 | L0.5 | L0.5 | L0.5 |
| Pounds Per Gal. | 7.171 | 7.106 | 7.119 | 7.162 |

The blend of nonionic surfactants is a blend of acidified sorbitan fatty acid esters, polyethoxylated derivatives of sorbitan fatty acid esters and alkylaryl polyethoxylated phosphate esters. The sorbitan fatty acid ester is acidified by addition of 2.5% by weight of the total blend of a 50% by weight solution of a weak organic acid such as citric acid. Other weak organic acids such as acetic and propionic acid could be used. Additional acidification and solubility enhancement can be obtained by the addition of about 3% by weight oleic acid to the acidified ester. The sorbitan fatty acid esters useful in this invention have the following general formula:

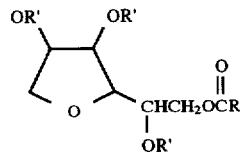

where R is $C_6$–$C_{20}$, R' is hydrogen or —C—R

Useful esters include sorbitan monolaurate, sorbitan monopalmitate, sorbitan monooleate, sorbitan monostearate, sorbitan trioleate, and sorbitan tristearate. Sorbitan trioleate is the preferred ester.

The polyethoxylated sorbitan ester component of the blend contains 20 moles of ethylene oxide and has a final HLB of 11.0. This component makes up about 75% by weight of the total blend. Polyethoxylated sorbitan esters which can be used in the blend have the following general formula:

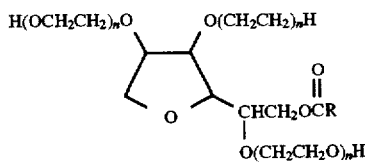

where $R_1$ is $C_6$–$C_{20}$ and n is 1 to 20. Suitable ethoxylated esters include those derived from sorbitan monolaurate (20 moles ethylene oxide), sorbitan monolaurate (4 EO), sorbitan monopalmitate (20 EO), sorbitan monostearate (20 EO), sorbitan monostearate (4 EO), sorbitan tristearate (20 EO), sorbitan monooleate (20 EO), sorbitan monooleate (5 EO) and sorbitan trioleate (20 EO).

The alkylaryl polyethoxylated phosphate esters useful in the compositions of the present invention are esters having the following formula:

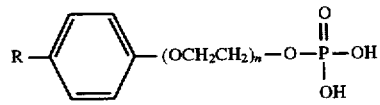

in which R is an alkyl group of 6 to 12, preferably 9 carbon atoms, n is 4 to 6. These esters are known, commercially available surfactants. The preferred ester is a nonyl phenol ethoxylate ester of phosphoric acid wherein n is 4.

Other ingredients which can be added to the homogeneous composition include propylene glycol, dipropylene glycol and petroleum distillates. Such additives are added only if needed and the amount added of each is 5% by weight or less. The compositions of the present invention are essentially nonaqueous which means that the amount of water in the compositions of this invention does not exceed 10% by weight of the total composition, preferably 8% by weight, most preferably 3% by weight. However, some water is typically present due to the presence of water in the surfactants.

Adjuvant compositions according to the present invention are prepared by acidifying the sorbitan fatty acid ester with a weak organic acid such as citric acid. The acidified ester is then mixed with the polyethoxylated sorbitan fatty acid ester to provide an emulsifier blend. The blend is added to the appropriate petroleum hydrocarbon oil. The buffering agent is added to the oil/emulsifier mixture with additional agitation to provide a clear solution. If necessary, water can be added in small increments, e.g., 0.25% by weight, but the amount added is kept to a minimum.

The adjuvant composition of this invention is useful with a broad range of pesticides where an oil concentration adjuvant is recommended. If applied properly, these adjuvant compositions can be used with fertilizer products and herbicides. Optimum applications and effects can be influenced by the crop, pest, spray equipment, spray volume, pressure, droplet size, spray mixture, environmental factors and other factors. Consequently, observation of the spray deposit is typically made and the adjuvant concentrations are adjusted accordingly. In mixing the adjuvant compositions with the pesticide or herbicide, the spray tank is filled one-half full with water and agitated. The pesticide and/or fertilizer is added as directed by labeling or in the following sequence: dry flowables or water dispersible granules, wettable powders, flowables, solutions and emulsifiable concentrates. The filling of the tank with water is continued and the adjuvant composition is added last and agitation is continued.

The pesticide or herbicide compositions containing the adjuvant compositions of the present invention can be applied by ground, aerial or aquatic spray equipment. In most cases, enough of the composition is applied to allow for adjustment of the spray pH to the desired range and uniform wetting and deposition of the spray on the leaf surfaces without undue runoff. For ground application, 1-4 pints are used in 20-100 gallons of spray solution per acre. Concentration should not exceed 1.5% v/v. For low volume aerial application, 2-8 fl. oz. per acre are typically used. In an aquatic application, 1-4 pints per acre are used not to exceed 1.5% v/v concentration.

The herbicide compositions containing the adjuvant compositions of the present invention include, but are not limited to, triazines, (such as atrazine or simazine), anilines, (such as trifluralin and pendimethalin), anilides, (such as propanil), phenoxys, such as 2,4-D), oximes, (such as sethoxydim). The insecticide compositions containing the adjuvant compositions of the present invention include, but are not limited to, organophosphates, (such as dimethoate and methyl parathion), carbamates, (such as carbaryl), and pyrethroids, (such as cyfluthrin and cypermethrin). The fungicide compositions containing the adjuvant compositions of the present invention include, but are not limited to, phthalamides, (such as captan), conazoles, (such as propiconazole).

EXAMPLES

Example 1

A mixture of 94.5 parts sorbitan trioleate and 3 parts oleic acid was heated to 60° F. and stirred continuously until the mixture was homogeneous. Two and one half parts of a 50% citric acid solution in water were added to the mixture sufficient agitation to obtain solution and/or dispersion of the aqueous acid. The final mixture provided an acidified sorbitan fatty acid ester. The mixture was then mixed at a 1:3 weight ratio with a polyethoxylated sorbitan trioleate containing 20 moles of ethylene oxide. The final emulsifier blend consisted of 75% by weight polyethoxylated sorbitan trioleate and 25% by weight acidified fatty acid ester. The blend was then added (18% by weight) to a paraffinic oil, SUN SPRAY 11N™ (supplied by Sun Oil Company), a 100 viscosity spray oil with a distillation range of 465°–471° C. The emulsifier blend and oil were agitated for 15 minutes utilizing a low speed prop type mixture. Two percent by weight of a phosphorylated nonyl phenol ethoxylate containing 5 moles of ethylene oxide was added to the emulsifier/oil mixture and the resulting composition was agitated for an additional 15 minutes. At the end of the blending period, the resulting composition was clear and free of turbidity. The resulting composition (Composition 1) had the following components:

| COMPONENT | % | FUNCTION |
| --- | --- | --- |
| PARAFFIN OIL | 80.0 | PESTICIDE ACTIVITY ENHANCEMENT |
| POE SORBITAN TRIOLEATE | 12.0 | EMULSIFIER FOR OIL-SURFACTANT FOR S.T. REDUCTION |
| SORBITAN TRIOLEATE | 2.0 | EMULSIFIER FOR OIL |
| OLEIC ACID | 2.0 | ACIDIFIER AND SOLUBILITY AID |
| POE ALKYL ARYL PHOSPHATE | 2.0 | ACIDIFIER AND BUFFERING AGENT |
| PROPYLENE GLYCOL | 1.5 | COUPLING AGENT FOR EMULSIFIER/OIL |
| CITRIC ACID (50) | 0.5 | ACIDIFIER |
| | 100.0 | |

*COMPOSITION MAY VARY DUE TO RAW MATERIALS

Comparative Example A

A composition (Composition A) having the composition shown below is prepared to show the need to use the sorbitan ester and the phosphate ester to obtain the advantages produced by the adjuvant compositions of the present invention.

| Ingredient | % |
| --- | --- |
| Paraffin Oil | 83.0 |
| 4 POE Sorbitan trioleate | 12.0 |
| Sorbitan trioleate | 1.5 |
| Propylene glycol | 2.0 |
| Water | 1.5 |
| | 100.0 |

The following comparison shows that when the phosphate ester is omitted, the performance of the above composition as a buffering agent is inferior to the performance of the adjuvant compositions of the present invention. The compositions are added to distilled water having a pH of 10.

| Composition with phosphate ester | | Composition without phosphate ester | |
|---|---|---|---|
| % volume | pH | % volume | pH |
| 0 | 10 | 0 | 10 |
| 0.25 | 6.5 | 0.25 | 8.0 |
| 0.50 | 4.5 | 0.50 | 8.0 |
| 0.75 | 4.0 | 0.75 | 7.8 |
| 1.00 | 3.5 | 1.00 | 7.8 |
| 1.50 | 3.4 | 1.50 | 7.8 |
| 1.75 | 3.3 | 1.75 | 7.5 |
| 2.00 | 3.2 | 2.00 | 7.5 |

Without the phosphate ester, the composition does not reduce the pH to the desired range of 4–6, or to the acidic range, and there is a loss of produce homogeneity because the components tend to separate upon standing.

Comparative Example B

The following composition (Composition B) provided a combination of paraffinic spray oil and phosphate ester without the sorbitan ester.

| Ingredient | % |
|---|---|
| Paraffin Oil (Sun Spray 11N$_{TM}$) | 83.0 |
| 4 POE Nonyl phenol | 12.0 |
| 4 POE alkyl aryl phosphate | 2.0 |
| Stearic acid | 1.0 |
| Oleic acid | 2.0 |
| | 100.0 |

Although the buffer performance was acceptable, the emulsion performance was very poor in comparison with the compositions of the present invention. The composition without the sorbitan ester was not stable and the components separated out upon standing.

Emulsion performance for agricultural formulations is usually evaluated by means of World Health Organization (WHO) method number SIF/31.R2. Utilizing this procedure in the evaluation of examples A+B produces the following results for a 5% by volume mix in 342 ppm water:

Emulsion Stability Performance (measured as amount of oil separated from the water/adjuvant mix in ml vs. time)

| SEPARATION OF COMPOSITION 1 | SEPARATION OF COMPOSITION A | SEPARATION OF COMPOSITION B | TIME IN MINUTES |
|---|---|---|---|
| 0 | 0 | 1.25 | 5 |
| 0 | 0 | 1.75 | 10 |
| 0 | trace | 2.25 | 15 |
| trace | trace | 2.25 | 20 |
| 0.5 | 0.25 | 2.25 | 25 |
| 1.0 | 1.0 | 2.25 | 30 |
| 1.0 | 1.0 | 2.25 | 45 |
| 1.0 | 1.0 | 2.25 | 60 |
| 1.0 | 1.0 | 2.25 | 120 |
| 1.5 | 1.0 | 2.25 | 24 |

The surfactant type and amount is selected based on emulsion stability performance. The tests are performed on the composition in combination with the buffering agent and spray oil. The guidelines below determine the degree of preference.

| Separation (Preferred) (ML) | Separation Most Preferred (ML) | Time in Minutes |
|---|---|---|
| 0 | 0 | 5 |
| trace | 0 | 15 |
| 1.00 | 0.5 | 30 |
| 1.50 | 1.00 | 45 |
| 1.75 | 1.00 | 60 |
| 2.00 | 1.00 | 120 |

Examples

| (2) Spray Oil | 80.00 |
|---|---|
| Nonyl Phenol Ethoxylate (6-mole) | 18.00 |
| Acetic Acid | 2.00 |
| | 100.00 |
| (3) Spray Oil | 80.00 |
| Nonyl Phenol Ethoxylate (5–6 mole) | 18.00 |
| Propionic Acid | 2.00 |
| | 100.00 |
| (4) Spray Oil | 80.00 |
| Nonyl Alcohol Ethoxylate (6 mole) | 18.00 |
| Acetic Acid | 2.00 |
| | 100.00 |
| (5) Spray Oil | 83.00 |
| Stearyl Alcohol Ethoxylate 4–5 mole | 15.00 |
| Acetic Acid | 1.00 |
| Lactic Acid | 1.00 |
| | 100.00 |
| (6) Spray Oil | 80.00 |
| Nonyl phenol Ethoxylate (5–6 mole) | 10.00 |
| Carboxylated alcohol ethoxylate (5 mole) | 8.00 |
| Acetic Acid | 2.00 |
| | 100.00 |
| (7) Spray Oil | 80.00 |
| Nonyl Phenol Ethoxylate (5–6 mole) | 10.00 |
| Acetic Acid | 2.00 |
| Carboxylated alcohol ethoxylate (5 mole) | 5.00 |
| Silicone Surfactant (Silvet L-77) | 3.00 |
| | 100.00 |
| (8) Spray Oil | 80.00 |
| Nonyl Phenol Ethoxylate | 10.00 |
| PEG Ester Ethoxylate (6 moles) | 5.00 |
| Acetic Acid | 1.00 |
| Citric Acid | .50 |
| Glutaric | .50 |
| Carboxylated alcohol ethoxylate (5 mole) | 3.00 |
| | 100.00 |

Additional Examples are as follows:

Example 9

A mixture of 50.0 parts methyl ester of soybean oil and 30.0 parts of a polyethoxylated isodecyl alcohol phosphate ester and 20.0 parts of a nonylphenol with 6 moles of ethylene oxide was stirred until the mixture was homogeneous.

At the conclusion of blending, the mixture was clear and free of turbidity. The resultant mixture (Composition 1) had the following components:

| Chemical Name | % | Function |
|---|---|---|
| Methyl esters of soybean oil | 50.0 | Pesticide Activity Enhancement |
| Polyethoxylated isodecyl alcohol phosphate ester | 30.0 | Buffering agent |
| Nonylphenol with 6 moles of ethylene oxide (EO) | 20.0 | Emulsifier |
| TOTAL | 100.0 | |

A composition (Composition A) having the composition shown below is prepared to show the need to use the phosphate ester to obtain the advantages produced by the adjuvant compositions of the present invention.

| Chemical Name | % | Function |
|---|---|---|
| Methyl esters of soybean oil | 80.0 | Pesticide Activity Enhancement |
| Nonylphenol with 6 moles of ethylene oxide | 20.0 | Emulsifier |
| TOTAL | 100.0 | |

The following comparison shows that when the phosphate ester is omitted, the performance of the above composition as a buffering agent is inferior to the performance of the adjuvant compositions of the present invention. The compositions are added to distilled water at the rate of 0.5% by volume. Each mixture with water is then agitated to ensure complete dispersion of the emulsified oil in water. These mixtures are then titrated with a 10% diethanolamine solution. The pH is monitored after additions of the diethanolamine titrant.

| Composition with phosphate ester | | Composition without phosphate ester | |
|---|---|---|---|
| % volume titrant | pH | % volume titrant | pH |
| 0 | 2.1 | 0 | 6.8 |
| 0.75 | 5.1 | 0.75 | 9.0 |
| 0.90 | 6.0 | 0.90 | 9.2 |
| 1.50 | 8.0 | 1.50 | 9.5 |

Without the phosphate ester, the composition does not reduce the pH to the desired range of 4–6. Furthermore, addition of an alkaline material to the mixture raises the pH of the mixture without the phosphate ester much more readily.

Furthermore, the composition without the emulsifier produces an oil-in-water emulsion which begins to produce creamy separation after only 1 hour. The phosphate ester produced a mini-emulsion which is stable for over 24 hours. Further Examples of the Patented Composition:

| | | |
|---|---|---|
| (10) Saponified soybean oil | 80.0% | |
| Nonylphenol with 6 moles EO | 18.0% | |
| Acetic Acid | 2.0% | |
| (11) Polybutenes with an average molecular weight of 320 | 80.0% | |
| Nonylphenol with 6 moles EO | 18.0% | |
| Acetic Acid | 2.0% | |
| (12) Soybean Oil | 80.0% | |
| Nonylphenol with 6 moles EO | 18.0% | |
| Acetic Acid | 2.0% | |
| (13) Oleic acid | 83.0% | |
| C10–12 alcohol with 6 moles EO | 15.0% | |
| Acetic Acid | 1.0% | |
| Lactic Acid | 1.0% | |
| (14) Methyl esters of soybean oil | 80.0% | |
| Nonylphenol with 6 moles EO | 10.0% | |
| Carboxylic acid ester of nonylphenol with 6 moles EO | 8.0% | |
| Acetic Acid | 2.0% | |
| (15) Methyl esters of soybean oil | 80.0% | |
| Nonylphenol with 6 moles EO | 10.0% | |
| Carboxylic acid ester of nonylphenol with 6 moles EO | 5.0% | |
| Acetic Acid | 2.0% | |
| Polyalkyleneoxide modified heptametyltrisiloxane | 3.0% | |

While there is shown and described herein certain specific structure embodying the invention, it will be manifest to those skilled in the art that various modifications and rearrangements of the parts maybe made without departing from the spirit and scope of the underlying inventive concept and that the same is not limited to the particular forms herein shown and described.

I claim:

1. A homogeneous, essentially nonaqueous adjuvant composition comprising:

(1) at least one spray oil selected from the group consisting of:
  (a) vegetable oils;
  (b) esterified fatty acids or blends thereof;
  (c) saponified fatty acids or blends thereof;
  (d) N,N-dimethylamide of the formula
  RCON(CH$_3$)$_2$
  wherein R is an alkyl chain derived from fatty acids having about 6 to about 18 carbon atoms;
  (e) polybutenes of the following formula

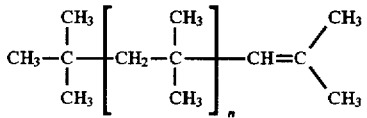

where n is a number from about 1 to about 50;
  (f) alpha or beta pinene,
  (g) thymol and
  (h) d-limonene, (2) a surfactant in an effective amount to provide emulsification of said composition and (3) a buffering agent wherein said buffering agent can also be the same ingredient as said oil or said surfactant and said buffering agent reduces the pH of said composition to about 7 or below.

2. The composition as claimed in claim 1, wherein said surfactant comprises at least one surfactant selected from the group consisting of
N-acyl sarcosines and sodium N-acyl sarcosinates,
alkylaryl polyethoxy phosphate ester,
alkylaryl polyethoxy carboxylate ester,
tristyrylphenol alkoxylate phosphate esters,
tristyrylphenol alkoxylate carboxylate esters,
phosphate esters of block copolymers of ethylene and propylene oxide and
alkylpolyglucosides.

3. The composition as claimed in claim 2, wherein said at least one spray oil is selected from the group consisting of
   (h) alpha or beta pinene,
   (i) thymol,
   (j) d-limonene and
   (k) jojoba bean oil.
4. The composition as claimed in claim 2, wherein said buffering agent is selected from the group consisting of:
   a) alkylaryl polyethoxy phosphate ester,
   b) $C_1$-$C_6$ carboxylic acids,
   c) $C_1$-$C_6$ dicarboxylic acids,
   d) phosphoric acid,
   e) citric acid,
   f) glutaric acid,
   g) gluconic acid,
   h) lactic acid,
   i) glycolic acid,
   j) acrylic acid,
   k) carboxylated alcohol ethoxylate of the formula
      R—O(CH$_2$CH$_2$O)$_x$H
      R is a carboxylic acid having from 1 to about 25 carbon atoms and x is from 1 to about 20 moles ethylene oxide.
   l) ethoxylated alkylphenol carboxylate esters;
   m) tristyrylphenol alkoxylate phosphate esters;
   n) tristyrylphenol alkoxylate carboxylate esters;
   o) fatty acids and blends thereof and
   p) phosphate esters of block copolymers of ethylene and propylene oxide.
5. The composition as claimed in claim 1, wherein said at least one spray oil is selected from the group consisting of
   (h) alpha or beta pinene,
   (i) thymol,
   (j) d-limonene and
   (k) jojoba bean oil.
6. The composition as claimed in claim 1, wherein said buffering agent is selected from the group consisting of:
   a) alkylaryl polyethoxy phosphate ester,
   b) $C_1$-$C_6$ carboxylic acids,
   c) $C_1$-$C_6$ dicarboxylic acids,
   d) phosphoric acid,
   e) citric acid,
   f) glutaric acid,
   g) gluconic acid,
   h) lactic acid,
   i) glycolic acid,
   j) acrylic acid,
   k) carboxylated alcohol ethoxylate,
   l) ethoxylated alkylphenol carboxylate esters;
   m) tristyrylphenol alkoxylate phosphate esters;
   n) tristyrylphenol alkoxylate carboxylate esters;
   o) fatty acids and blends thereof and
   p) phosphate esters of block copolymers of ethylene and propylene oxide.
7. The composition as claimed in claim 1, wherein said buffering agent comprises fatty acids and blends thereof or phosphate esters of block copolymers of ethylene and propylene oxide.

8. The composition as claimed in claim 1, wherein said surfactant comprises at least one surfactant selected from the group consisting of
   (a) fatty alkanolamides of the formula

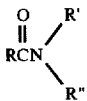

wherein R is a $C_6$-$C_{25}$ alkyl group; R and R" are the same or different and are independently selected from the group consisting of hydrogen, —CH$_2$CH$_2$OH and —CH$_2$—CH—OH,

—CH$_2$—CH—OH
           |
           CH$_3$ (b) PEG esters of the formula

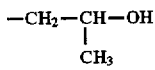

wherein R$^2$ is a $C_2$-$C_{25}$ fatty alkyl, R$^3$ is a $C_2$-$C_{25}$ fatty alkyl or hydrogen and m is a number from 1 to 100,
   (c) silicone surfactants of the formula

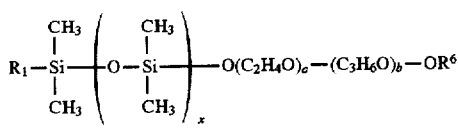

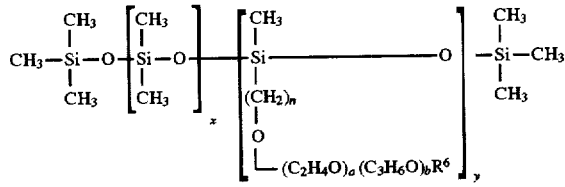

wherein R$_1$ and R$^6$ independently from one another are hydrogen, alkyl having from 1 to about 20 carbon atoms, or an alkyl ester group having 1 to 20 carbon atoms, x is a number from about 1 to about 100, y is a number from about 1 to about 5, a is a number from about 3 to about 25, b is a number from about 0 to about 25, and
   (d) ethoxylated fatty acids

wherein R$^7$ is a $C_6$-$C_{25}$ alkyl group, p is a number from 1 to 100.
   (e) alkyl ethoxylates
      R$^8$O(CH$_2$CH$_2$O)$_q$H
      wherein R$^8$ is alkyl group and q is a number from 1 to 100.

(f) alkylphenol ethoxylates

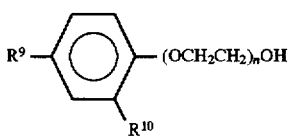

wherein $R^9$ is hydrogen or $C_1$–$C_{20}$ alkyl, $R^{10}$ is hydrogen or $C_1$–$C_{20}$ alkyl and n is a number from 1 to 100.

(g) polypropylene glycols

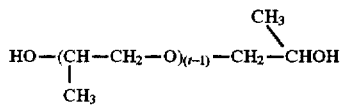

wherein t is a number from 1 to about 100.

(h) amine ethoxylates

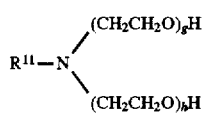

wherein g and h are identical or different and are numbers from 1 to about 100 and R" is a $C_1$–$C_{25}$ alkyl.

(i) tristyrylphenol alkoxylate,
(j) N-acyl sarcosines and sodium N-acyl sarcosinates,
(k) alkylaryl polyethoxy phosphate ester,
(l) alkylaryl polyethoxy carboxylate ester,
(m) tristyrylphenol alkoxylate phosphate esters,
(n) tristyrylphenol alkoxylate carboxylate esters,
(o) phosphate esters of block copolymers of ethylene and propylene oxide and
(p) alkylpolyglucosides.

9. The composition as claimed in claim 8, wherein said at least one spray oil is selected from the group consisting of (h) alpha or beta pinene,
(i) thymol,
(j) d-limonene and
(k) jojoba bean oil.

10. The composition as claimed in claim 8, wherein said buffering agent is selected from the group consisting of:
a) alkylaryl polyethoxy phosphate ester,
b) $C_1$–$C_6$ carboxylic acids,
c) $C_1$–$C_6$ dicarboxylic acids,
d) phosphoric acid,
e) citric acid,
f) glutaric acid,
g) gluconic acid,
h) lactic acid,
i) glycolic acid,
j) acrylic acid,
k) carboxylated alcohol ethoxylate of the formula
R—O(CH$_2$CH$_2$O)$_x$H
R is a carboxylic acid having from 1 to about 25 carbon atoms and x is from 1 to about 20 moles ethylene oxide,
l) ethoxylated alkylphenol carboxylate esters;
m) tristyrylphenol alkoxylate phosphate esters;
n) tristyrylphenol alkoxylate carboxylate esters;
o) fatty acids and blends thereof and
p) phosphate esters of block copolymers of ethylene and propylene oxide.

11. An insecticide comprising the adjuvant composition as claimed in claim 1.

12. An agricultural composition comprising a herbicide and the homogeneous, essentially nonaqueous adjuvant composition as claimed in claim 1.

13. The agricultural composition as claimed in claim 12, wherein the herbicide is propanil.

14. An agricultural composition comprising a fungicide and the homogeneous, essentially nonaqueous adjuvant composition as claimed in claim 1.

15. A homogeneous, essentially nonaqueous adjuvant composition comprising:

(1) at least one spray oil is selected from the group consisting of:
  (a) vegetable oils;
  (b) esterified fatty acids or blends thereof;
  (c) saponified fatty acids or blends thereof;
  (d) N,N-dimethylamide of the formula
  RCON(CH$_3$)$_2$
  wherein R is an alkyl chain derived from fatty acids having about 6 to about 18 carbon atoms;
  (e) polybutenes of the following formula

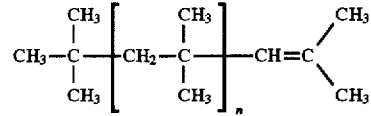

where n is a number from about 1 to about 50;
  (f) alpha or beta pinene,
  (g) thymol,
  (h) d-limonene and
  (i) spray oil having a UR value of at least about 85%.

(2) surfactant comprises at least one surfactant selected from the group consisting of
  (a) fatty alkanolamides of the formula

wherein R is a $C_6$–$C_{25}$ alkyl group; R' and R" are the same or different and are independently selected from the group consisting of hydrogen, —CH$_2$CH$_2$OH and —CH$_2$—CH—OH,

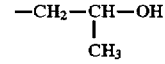

(b) PEG esters of the formula

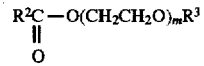

wherein $R^2$ is a $C_2$–$C_{25}$ fatty alkyl, $R^3$ is a $C_2$–$C_{25}$ fatty alkyl or hydrogen and m is a number from 1 to 100.

(c) silicone surfactants of the formula

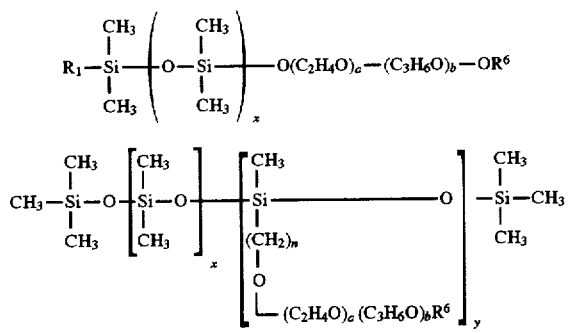

wherein $R_1$ and $R^6$ independently from one another are hydrogen, alkyl having from 1 to about 20 carbon atoms, or an alkyl ester group having 1 to 20 carbon atoms, x is a number from about 1 to about 100, y is a number from about 1 to about 5, a is a number from about 3 to about 25, b is a number from about 0 to about 25, and (d) ethoxylated fatty acids

wherein $R^7$ is a $C_6$–$C_{25}$ alkyl group, p is a number from 1 to 100, (e) alkyl ethoxylates
$R^8O(CH_2CH_2O)_qH$
wherein $R^8$ is alkyl group and q is a number from 1 to 100.

(f) alkylphenol ethoxylates

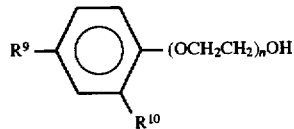

wherein $R^9$ is hydrogen or $C_1$–$C_{20}$ alkyl, $R^{10}$ is hydrogen or $C_1$–$C_{20}$ alkyl and n is a number from 1 to 100, (g) polypropylene glycols

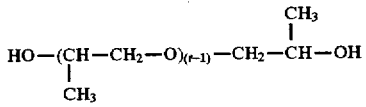

wherein t is a number from 1 to about 100, (h) amine ethoxylates

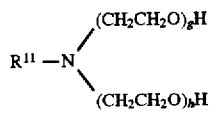

wherein g and h are identical or different and are numbers from 1 to about 100 and $R^{11}$ is a $C_1$–$C_{25}$ alkyl (i) tristyrylphenol alkoxylate,
(j) N-acyl sarcosines and sodium N-acyl sarcosinates,
(k) alkylaryl polyethoxy phosphate ester,
(l) alkylaryl polyethoxy carboxylate ester,
(m) tristyrylphenol alkoxylate phosphate esters,
(n) tristyrylphenol alkoxylate carboxylate esters,
(o) phosphate esters of block copolymers of ethylene and propylene oxide and
(p) alkylpolyglucosides in an effective amount to provide emulsification of said composition and (3) a buffering agent wherein said buffering agent can also be the same ingredient as said oil or said surfactant and said buffering agent reduces the pH of said composition to about 7 or below.

16. The composition as claimed in claim 15, wherein said surfactant comprises at least one surfactant selected from the group consisting of N-acyl sarcosines and sodium N-acyl sarcosinates, alkylaryl polyethoxy phosphate ester, alkylaryl polyethoxy carboxylate ester, tristyrylphenol alkoxylate phosphate esters, tristyrylphenol alkoxylate carboxylate esters, phosphate esters of block copolymers of ethylene and propylene oxide and alkylpolyglucosides.

17. The composition as claimed in claim 15, wherein said buffering agent is selected from the group consisting of:

a) alkylaryl polyethoxy phosphate ester,
b) $C_1$–$C_6$ carboxylic acids,
c) $C_1$–$C_6$ dicarboxylic acids,
d) phosphoric acid,
e) citric acid,
f) glutaric acid,
g) gluconic acid,
h) lactic acid,
i) glycolic acid,
j) acrylic acid,
k) carboxylated alcohol ethoxylate,
l) ethoxylated alkylphenol carboxylate esters;
m) tristyrylphenol alkoxylate phosphate esters;
n) tristyrylphenol alkoxylate carboxylate esters;
o) fatty acids and blends thereof and
p) phosphate esters of block copolymers of ethylene and propylene oxide.

18. The composition as claimed in claim 15, wherein said buffering agent comprises fatty acids and blends thereof or phosphate esters of block copolymers of ethylene and propylene oxide.

19. The composition as claimed in claim 18, wherein said surfactant comprises ethoxylated fatty acids.

20. A homogeneous, essentially nonaqueous adjuvant composition comprising:

at least one spray oil is selected from the group consisting of:
(a) vegetable oils;
(b) fatty acids and blends thereof;
(c) esterified fatty acids or blends thereof;
(d) saponified fatty acids or blends thereof;
(e) N,N-dimethylamide of the formula
$RCON(CH_3)_2$
wherein R is an alkyl chain derived from fatty acids having about 6 to about 18 carbon atoms;

(f) polybutenes of the following formula $$CH_3-\underset{\underset{CH_3}{|}}{\overset{\overset{CH_3}{|}}{C}}-\left[CH_2-\underset{\underset{CH_3}{|}}{\overset{\overset{CH_3}{|}}{C}}\right]_n-CH=C\diagup\begin{matrix}CH_3\\\\CH_3\end{matrix}$$

where n is a number from about 1 to about 50;
(h) alpha or beta pinene,
(i) thymol,
(j) d-limonene
(k) spray oil having a UR value of at least about 85%,
(2) surfactant comprises at least one surfactant selected from the group consisting of
(a) fatty alkanolamides of the formula $$RC\overset{\overset{O}{\|}}{N}\diagup\begin{matrix}R'\\\\R''\end{matrix}$$

wherein R is a $C_6$–$C_{25}$ alkyl group; R and $R^{11}$ are the same or different and are independently selected from the group consisting of hydrogen, —$CH_2CH_2OH$ and —$CH_2$—CH—OH,

—$CH_2$—CH—OH
         |
         $CH_3$ (b) PEG esters of the formula $$R^2C\overset{\overset{}{\|}}{\underset{O}{}}-O(CH_2CH_2O)_mR^3$$

wherein $R^2$ is a $C_2$–$C_{25}$ fatty alkyl, $R^3$ is a $C_2$–$C_{25}$ fatty alkyl or hydrogen and m is a number from 1 to 100, (c) silicone surfactants of the formula $$R_1-\underset{\underset{CH_3}{|}}{\overset{\overset{CH_3}{|}}{Si}}-\left(O-\underset{\underset{CH_3}{|}}{\overset{\overset{CH_3}{|}}{Si}}\right)_x-O(C_2H_4O)_a-(C_3H_6O)_b-OR^6$$

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_x-\left[\underset{\underset{\underset{(C_2H_4O)_a(C_3H_6O)_bR^6}{|}}{\overset{\overset{}{O}}{|}}}{\overset{\overset{CH_3}{|}}{\underset{(CH_2)_n}{Si}}}-O\right]_y-\underset{\underset{CH_3}{|}}{\overset{\overset{CH_3}{|}}{Si}}-CH_3$$

wherein $R_1$ and $R^6$ independently from one another are hydrogen, alkyl having from 1 to about 20 carbon atoms, or an alkyl ester group having 1 to 20 carbon atoms, x is a number from about 1 to about 100, y is a number from about 1 to about 5, a is a number from about 3 to about 25, b is a number from about 0 to about 25, (d) polypropylene glycols $$HO-(CH-CH_2-O)_{(t-1)}-CH_2-CH-OH$$
$$\phantom{HO-(}|\phantom{CH-CH_2-O)_{(t-1)}-CH_2-}|$$
$$\phantom{HO-(}CH_3\phantom{CH-CH_2-O)_{(t-1)}-CH_2-}CH_3$$

wherein t is a number from 1 to about 100,
(e) amine ethoxylates $$R^{11}-N\diagup\begin{matrix}(CH_2CH_2O)_gH\\\\(CH_2CH_2O)_hH\end{matrix}$$

wherein g and h are identical or different and are numbers from 1 to about 100 and $R^{11}$ is a $C_1$–$C_{25}$ alkyl (f) tristyrylphenol alkoxylate,
(g) N-acyl sarcosines and sodium N-acyl sarcosinates,
(h) alkylaryl polyethoxy phosphate ester,
(i) alkylaryl polyethoxy carboxylate ester,
(j) tristyrylphenol alkoxylate phosphate esters,
(k) tristyrylphenol alkoxylate carboxylate esters,
(l) phosphate esters of block copolymers of ethylene and propylene oxide and
(m) alkylpolyglucosides in an effective amount to provide emulsification of said composition and
(3) a buffering agent wherein said buffering agent can also be the same ingredient as said oil or said surfactant and said buffering agent reduces the pH of said composition to about 7 or below.

21. The composition as claimed in claim 20, wherein said buffering agent comprises fatty acids and blends thereof and spray oil comprises fatty acids and blends thereof.

22. A homogeneous, essentially nonaqueous adjuvant composition comprising a spray oil having a minimum of 85% of unsulfonated residue value, at least one surfactant selected from the group consisting of (a) fatty alkanolamides of the formula $$RC\overset{\overset{O}{\|}}{N}\diagup\begin{matrix}R'\\\\R''\end{matrix}$$

wherein R is a $C_6$–$C_{25}$ alkyl group; R' and R" are the same or different and are independently selected from the group consisting of hydrogen, —$CH_2CH_2OH$ and —$CH_2$—CH—OH,

—$CH_2CH$—OH
         |
         $CH_3$ (b) PEG esters of the formula $$R^2C\overset{\overset{}{\|}}{\underset{O}{}}-O(CH_2CH_2O)_mR^3$$

wherein $R^2$ is a $C_2$–$C_{25}$ fatty alkyl, $R^3$ is a $C_2$–$C_{25}$ fatty alkyl or hydrogen and m is a number from 1 to 100, (c) silicone surfactants of the formula $$R_1-\underset{\underset{CH_3}{|}}{\overset{\overset{CH_3}{|}}{Si}}-\left(O-\underset{\underset{CH_3}{|}}{\overset{\overset{CH_3}{|}}{Si}}\right)_x-O(C_2H_4O)_a-(C_3H_6O)_b-OR^6$$

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_x-\left[\underset{\underset{\underset{\underset{(C_2H_4O)_a(C_3H_6O)_bR^6}{|}}{O}}{(CH_2)_n}}{\overset{\overset{CH_3}{|}}{Si}}-O\right]_y-\underset{\underset{CH_3}{|}}{\overset{\overset{CH_3}{|}}{Si}}-CH_3$$

wherein $R_1$ and $R^6$ independently from one another are hydrogen, alkyl having from 1 to about 20 carbon atoms, or an alkyl ester group having 1 to 20 carbon atoms, x is a number from about 1 to about 100, y is a number from about 1 to about 5, a is a number from about 3 to about 25, b is a number from about 0 to about 25, and (d) ethoxylated fatty acids $$R^7\overset{\overset{O}{\|}}{C}-O(CH_2CH_2O)_pH$$

wherein $R^7$ is a $C_6$–$C_{25}$ alkyl group, p is a number from 1 to 100, (e) alkyl ethoxylates
$R^8O(CH_2CH_2O)_qH$
wherein $R^8$ is alkyl group and q is a number from 1 to 100, (f) alkylphenol ethoxylates $$R^9-\underset{\underset{R^{10}}{|}}{\bigcirc}-(OCH_2CH_2)_nOH$$

wherein $R^9$ is hydrogen or $C_1$–$C_{20}$ alkyl, $R^{10}$ is hydrogen or $C_1$–$C_{20}$ alkyl and n is a number from 1 to 100, (g) polypropylene glycols $$HO-(CH-CH_2-O)_{(t-1)}-CH_2-\underset{\underset{CH_3}{|}}{\overset{\overset{CH_3}{|}}{CH}}-OH$$

wherein t is a number from 1 to about 100, (h) amine ethoxylates $$R^{11}-N\underset{\diagdown (CH_2CH_2O)_hH}{\diagup (CH_2CH_2O)_gH}$$

wherein g and h are identical or different and are numbers from 1 to about 100 and $R^{11}$ is a $C_1$–$C_{25}$ alkyl, (i) tristyrylphenol alkoxylates and (j) N-acyl sarcosines and sodium N-acyl sarcosinates, (k) alkylaryl polyethoxy phosphate ester, (l) alkylaryl polyethoxy carboxylate ester, (m) tristyrylphenol alkoxylate phosphate esters, (n) tristyrylphenol alkoxylate carboxylate esters, (o) phosphate esters of block copolymers of ethylene and propylene oxide and (p) alkylpolyglucosides in an effective amount to provide emulsification of said composition and (3) a buffering agent wherein said buffering agent can also be the same ingredient as said oil or said surfactant and said buffering agent reduces the pH of said composition to about 7 or below and wherein said surfactant is mixed with sorbitan fatty acid ester and/or a polyethoxylated derivative of a sorbitan fatty acid ester.

\* \* \* \* \*